United States Patent [19]
Sudge et al.

[11] Patent Number: 6,121,024
[45] Date of Patent: Sep. 19, 2000

[54] HALOPHILIC PSEUDOMONAS STRAIN HAVING ACCESSION NO.NCIM 5109 (ATCC 55940) AND A PROCESS FOR PREPARING D(-)N-CARBAMOYLPHENYLGLYCINE USING SAID STRAIN

[76] Inventors: Sandhya Suresh Sudge; Kulbhushan Balwant Bastawade; Digamber Vitthal Gokhale; Rohini Ramesh Joshi; Uttam Ramrao Kalkote; Thottapillil Ravindranathan, all of National Chemical Laboratory, Pune-411 008, Maharashtra, India

[21] Appl. No.: 09/052,391

[22] Filed: Mar. 31, 1998

[30] Foreign Application Priority Data

Jul. 17, 1997 [IN] India .............................. 1997/DEL/97

[51] Int. Cl.[7] .............................. C12P 13/04; C12N 1/20
[52] U.S. Cl. ..................... 435/106; 435/253.3; 435/874
[58] Field of Search ................................ 435/253.3, 874, 435/106

[56] References Cited

U.S. PATENT DOCUMENTS 4,248,967  2/1981  Viglia et al. .............................. 435/106
4,418,146  11/1983  Lungershausen et al. .............. 435/106

OTHER PUBLICATIONS

Gokhale et al "Enzyme & Microbial Techn." 18:353–357 (1996).

Sudge et al "Production of D–Hydantoinase by Halophilic Pseudomonas SP. NCIM 5109" Appl. Microbiol Biotechn.(1998) 49: pp. 594–599.

*Primary Examiner*—Herbert J. Lilling
*Attorney, Agent, or Firm*—Ladas & Parry

[57] ABSTRACT

The present invention relates to a process for the preparation of D(-)N-carbamoylphenylglycine, by growing Pseudomonas sp deposited at National Collection of Industrial Microorganisms, Pune, India and at American Type Cultural Centre, Rockville, U.S.A and afforded accession No. ATCC 55940 in a conventional nutrient, medium, suspending the cells in alkaline buffer containing buffer, acidifying the broth to obtain the product.

8 Claims, No Drawings

HALOPHILIC PSEUDOMONAS STRAIN HAVING ACCESSION NO.NCIM 5109 (ATCC 55940) AND A PROCESS FOR PREPARING D(-)N-CARBAMOYLPHENYLGLYCINE USING SAID STRAIN

FIELD OF THE INVENTION

This invention relates to a novel halophilic Pseudomonas strain designated as NCIM 5109 and a novel process for the preparation of D(-)N-carbamoylphenylglycine. More particularly it relates to the process for the preparation of the compound using hydantoinase enzyme. The hydantoinase enzyme used in the process of the present invention is made available by halophilic bacterial strain.

BACKGROUND OF THE INVENTION

Optically active D-armino acids like p-hydroxyphenylglycine and D-phenylglycine are widely used as intermediates in pharmaceutical filed for the synthesis of semisynthetic antibiotics, peptide hormones, pyrethroids and pesticides. A chemoenzymatic route for the synthesis of various D-amino acids involves the conversion of DL-5-monosubstituted hydantoins to D-amino acids via N-carbamoyl D-amino acid by producing aerobic microorganisms [Takahashi, S., Ohashi, T., Kii, Y., Kumagai, H. and Yamada, H. (1979), J. Ferment. Technol., 57, 328–332; Yokozeki, K., Nakamori, S., Eguchi, C., Yamada, K. and Mitsugi, K. (1987). Agric. Biol. chelm. 51, 355–362]. In this process a DL-5-substituted hydantoin is asymmetrically hydrolyzed to the N-carbamoyl-D-amino acid using D-specific hydantoinase (dihydropyrimidinase, EC 3.5.2.2) and the product is further chemically converted to the corresponding D-amino acids under acidic conditions.

Much attention has been directed towards the isolation, screening and selection of D-hydantoinase producing microbes [Morin, A., Hummel, W. and Kula, M. R. (1987), J. Gen Microbiol.133, 1201–1207; Kim D. M. and Kim, H. S. (1993), Enzyme Microb Technol. 15, 530–534; Kalkote, U. R., Joshi, R. R., Joshi, R. A., Ravindranathan, T., Bastawde, K. B., Gokhale, D. V. Patil, S. G., Jogdand. V. V., Gaikwad, B. G. and Nene, S. (1993) Indian Patent No. 199/DEL/1993; Gokhale, D. V., Bastawde, K. B., Patil, S. G., Kalkote, U. R., Joshi, R. R., Joshi, R. A., Ravindranathan, T., Jogdand, V. V., Gaikwad, B. G. and Nene, S. (1996). Enzyme Microb. Technl. 18, 353–357] and the characterization of the kinetic properties of the enzyme [Runser, S. M. and Ohleyer, E. (1990), Biotechnolgy Lett. 12, 259–264; Morin, A., Leblanc, D., Paleczek, A., Hummel, W. and Kula, M. R.(1990), J. Biotechnol 16, 37–48; Ogawa, J., Kaimura, T., Yamada, H. and Shinizu, S. (1994), FEMS Microbiol Lett. 122, 44–60]. One of the main problems associated with the use of enzymes for biocatalysis is their stability. A thermophilic bacterium Bacillus stearothermophilus SD-1 showing high thermostability and activity of D-hydantoinase was isolated and the enzyme was purified to its homogeneity [Lee, S. G., Lee, D. C., Hong, S. P., Sung, M. H. and Kim H. S. (1995). Appl. Microbiol. Biotechnol. 43, 270–276].

SUMMARY OF THE INVENTION

The inventors have directed their research to the screening of nearly 300 bacterial strains isolated from sea water for hydantoinase production which resulted in identifying ten strains possessing hydantoinase activity. One of the ten selected strains that showed highest hydantoinase activity was found to be halophillic Pseudomonas sp. M-1 according to preliminary studies on morphological and physiological characteristics. The strain could grow well in medium containing high salt concentration (>7%) and was able to produce 5–6% D(-)N-carbamoylphenylglycine within 10–15 hrs. The strain has been deposited in National Collection of Industrial Microorganisms (NCIM), Pune, under accession number NCIM 5109. The strain was also deposited at the American Type Culture Collection, 10801 University Boulevard, Manassas, Va. 20110 on Nov. 2, 1999 under accession number PTA-901.

The object of the present invention therefore is to provide an improved process for the preparation of D(-)N-carbamoylphenylglycine using halophillic bacterial strain, Pseudomonas sp. NCIM 5109.

DESCRIPTION OF THE INVENTION

Accordingly, the present invention provides a process for the preparation of D(-)n-carbamoylphenylglycine which comprises growing halophilic bacterial strain NCIM 5109 in a conventional nutrient medium, for a period of 18 to 36 hrs. at a temperature ranging between 20 to 35 ° C. separating the cells by known methods, suspending the cells in alkaline buffer containing the substrate for a period in the range of 16 to 24 hrs. under shaking conditions, at a temperature ranging between 20 to 35° C., harvesting the reaction mixture and separating the broth by conventional methods, acidifying the broth to obtain the solid product.

In one of the embodiments of the present invention halophilic strain used for the production of the enzyme is isolated from the marine environments designated as Pseudomonas sp.

In another embodiment of the present invention the buffer used is of pH 8 to 10.

In another embodiment of the present invention strength of the buffer ranges between 0.2 to 0.5 M for Tris buffer.

In still another embodiment the strength of the bicarbonate buffer ranges between 0.1 to 0.3 M.

What is claimed is:

1. An isolated halophilic bacterial strain of Pseudomonas for use in the preparation of D(-)N-carbamoylphenylglycine, said strain being desigated as NCIM 5109 and being on deposit at the American Type Culture Collection under accession number PTA-901.

2. A process for the preparation of D(-)N-carbamoylphenylglycine which comprises growing halophilic bacterial strain Pseudomonas sp. having accession No.NCIM 5109 (ATCC 55940) deposited at National Collection to Industrial Microorganisms (NCIM), Pune, in the Nutrient broth medium, for a period of 20 to 36 hrs. at a temperature ranging between 20 to 30° C., separating the cells by conventional methods, suspending the cells in alkaline buffer containing the substrate for a period in the range of 16 to 24 hrs. under shaking conditions, at a temperature ranging between 25 to 30° C., harvesting the reaction mixture and separating the broth by conventional methods, acidifying the broth to obtain the solid product.

3. A process as claimed in claim 2 wherein the halophilic strain used for the production of the enzyme is isolated from the marine environments, designated as Pseudomonas sp. M-1 NCIM 5109 (ATCC 55940).

4. A process as claimed in claim 2 wherein the buffer used is of pH 8 to 10.

5. A process as claimed in claim 2 wherein the strength of the buffer ranges between 0.2 to 0.5M for Tris buffer.

6. A pocess as claimed in claim 2, wherein the strength of the bicarbonate buffer ranges between 0.1 to 0.30M.

7. A process as claimed in claims 2 wherein the acid used for acidifying the harvested broth is selected from hydrochloric acid, trichloroacetic acid, sulphuric acid.

8. A process as claimed in claim 2 wherein the substrate used is selected from DL-5 phenylhyadontoin or DL-5-hydroxyphenylhydantoin.

* * * * *